(12) United States Patent
Snowball

(10) Patent No.: US 7,173,255 B2
(45) Date of Patent: Feb. 6, 2007

(54) IRRADIATION DEVICE

(76) Inventor: Malcolm Robert Snowball, 4 The Gables, The Plain, Epping Essex (GB) CM16 6TW ( * ) Notice: Subject to any disclaimer, the term of this patent is extended or adjusted under 35 U.S.C. 154(b) by 0 days.

(21) Appl. No.: 11/126,416

(22) Filed: May 11, 2005

(65) Prior Publication Data

US 2005/0253086 A1 Nov. 17, 2005

(30) Foreign Application Priority Data

May 13, 2004 (GB) .................... 0410607

(51) Int. Cl.
 C02F 1/32 (2006.01)
 C02F 9/00 (2006.01)
 B01D 29/23 (2006.01)
 B01D 29/27 (2006.01)
(52) U.S. Cl. .............. 250/455.11; 210/198.1; 210/205; 210/748; 422/186.3
(58) Field of Classification Search ........... 250/435, 250/455.11
 See application file for complete search history.

(56) References Cited

U.S. PATENT DOCUMENTS

| 4,141,830 A | 2/1979 | Last |
| 4,968,489 A * | 11/1990 | Peterson .................. 422/186.3 |
| 5,935,431 A | 8/1999 | Korin |
| 6,303,087 B1 | 10/2001 | Wedekamp |
| 6,328,884 B1 * | 12/2001 | Kunkel .................... 210/198.1 |
| 6,814,861 B2 * | 11/2004 | Husain et al. ........... 210/257.2 |
| 2001/0032659 A1 | 10/2001 | Wang et al. |

FOREIGN PATENT DOCUMENTS

| DE | 198 46 380 A1 | 4/2000 |
| EP | 0306301 A1 | 3/1989 |
| JP | 07-100461 | 4/1995 |
| WO | WO 95/09814 A1 | 4/1995 |

* cited by examiner

Primary Examiner—David Vanore
(74) Attorney, Agent, or Firm—Edwin D. Schindler

(57) ABSTRACT

An irradiation device, for example a UV irradiation device for disinfecting waste water, is arranged to emit radiation from a source and through an outer wall which is permeable to fluid. Means are provided for varying the fluid pressure behind the inner surface of the outer wall, to cause fluid to permeate through it, either inwardly or outwardly. The arrangement serves to maintain the outer surface of the permeable wall clear of contaminants.

9 Claims, 2 Drawing Sheets

FIGURE I

IRRADIATION DEVICE

Figure 1:
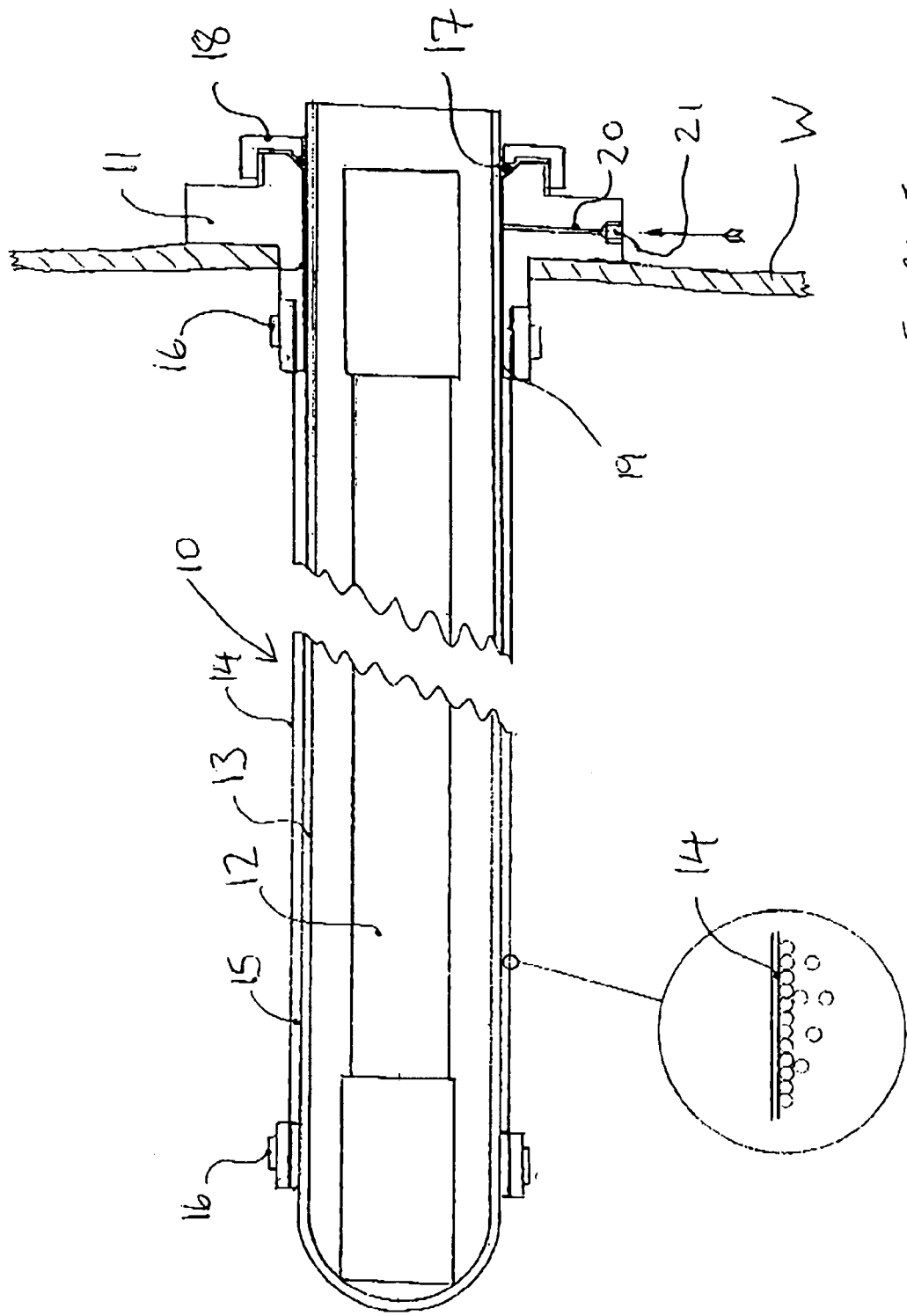

The present invention relates to an irradiation device and more particularly but not solely to an ultra-violet irradiation device for disinfecting fluids such as waste water.

It is well known that high-intensity ultra-violet (UV) light has germicidal properties. However, a problem of disinfecting waste water using this technique is that it is difficult to keep the outer surface of the UV lamp clean and accordingly the radiation becomes substantially attenuated to a level where it become ineffective.

Known UV disinfection devices generally comprise a mercury arc lamp contained within a quartz sleeve. The lamps are typically of the low or medium pressure type, and radiate wavelengths in the UVC wave band: UVC wavelengths of 240–280 nm cause disruptions in DNA sequences which lead to death or inactivation of microorganisms. This technology is an extremely effective method of disinfection provided the radiation is allowed to radiate throughout the whole volume of waste water.

In order to disinfect a fluid such as waste water, a mercury arc lamp contained within a quartz sleeve is submerged into the waste water and the lamp irradiates the waste water through the quartz sleeve. However, the waste water contains debris and contaminants which quickly foul the quartz tube by adhering to it. This effectively attenuates the UVC radiation and causes some regions of the fluid within the treatment chamber to be untreated.

In order to overcome this problem, it is known to provide a mechanical cleaning device comprising a wiper which traverses the quartz sleeve and wipes the outer surface thereof. Such cleaning devices are often unreliable because they cannot access all of the contours of the tube surface. In addition, the wipers merely smear the fouling across the outer surface of the quartz sleeve rather than cleaning it sufficiently. Also, the complexity of the devices often causes frequent failures, particularly since the devices are continuously immersed in water.

I have now devised an irradiation device which alleviates the above-mentioned problems.

In accordance with this invention there is provided an irradiation device arranged to emit radiation through an outer wall thereof formed of a material which is transparent or substantially transparent to the wavelength(s) of the emitted radiation, said outer wall being formed of a material which is permeable to fluid, the device further comprising means for varying the fluid pressure behind the inner surface of said wall to cause fluid to permeate through the wall.

In use, when the fluid pressure behind the inner surface of the permeable wall is greater than the pressure of the medium surrounding the irradiation device, the fluid permeates from inside the device through the wall and into the medium.

This continuous flow of fluid through the pores of the permeable wall, and hence over the outer surface of the wall, keeps the outer surface of the wall clean by preventing contaminants and fouling approaching its surface. The action also helps to purge accumulated contaminants, Advantageously, when the fluid pressure behind the inner surface of the permeable wall is lower than the pressure of the medium surrounding the irradiation device, the medium permeates from outside the device through the wall and into the device.

This continuous flow of medium through the pores of the permeable wall acts to filter contaminants from the medium. The contaminants are retained on the Outer surface of the wall where they are irradiated and any microorganisms contained therein are killed.

Preferably the fluid pressure behind the inner surface of the permeable wall can be varied between a pressure which is greater than the pressure of the medium surrounding the irradiation device and a pressure which is lower than the pressure of the medium surrounding the irradiation device. In this manner, any contaminants retained on the outer surface of the wall by the aforementioned filtering action can be removed by applying pressure which is greater than the pressure of the surrounding medium, effectively to provide a back washing action.

Preferably the device comprises a lamp at least partially disposed within a chamber, said permeable wall forming at least a portion of the wall of the chamber, and said means for varying the fluid pressure behind the inner surface of said permeable wall are arranged to vary the pressure within the chamber.

Preferably the lamp is elongate, the wall of the chamber comprising a sleeve surrounding said lamp.

Preferably the porous wall is formed of PTFE, preferably Teflon® FEP.

Preferably the chamber is sealed against the ingress of the medium surrounding the device.

Preferably the lamp extends from a body of the device, the body comprising a fluid flow duct which extends between the chamber and said means for varying the fluid pressure.

Preferably means are provided for adding a cleaning fluid, such as a fluid containing chlorinated or acidic elements, to the pressurised fluid. The cleaning fluid reacts with the surface of the permeable wall of the device, thereby adding an additional cleansing action.

Preferably the pressurized fluid is heated or cooled to control the lamp temperature.

Preferably the pressurised fluid is filtered to prevent a build up of contaminants behind the permeable wall.

Figure 2:
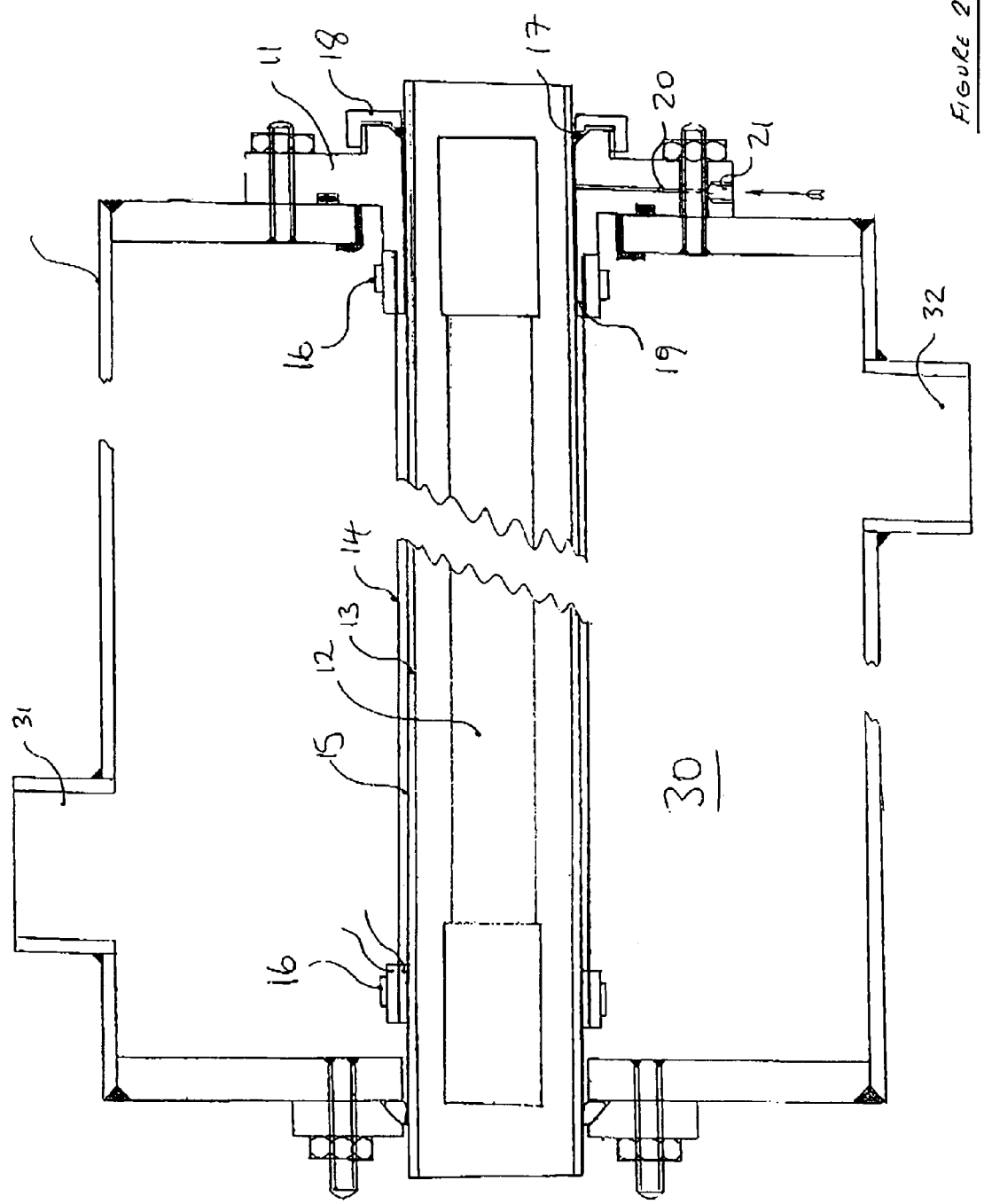

Embodiments of this invention will now be described by way of examples only and with reference to the accompanying drawings, in which:

FIG. 1 is longitudinal sectional view through an embodiment of a UV disinfection lamp device in accordance with this invention; and FIG. 2 is longitudinal sectional view through an alternative embodiment of a UV disinfection lamp device in accordance with this invention.

Referring to the FIG. 1 of the drawings, there is shown a UV disinfection lamp device comprising an elongate UV lamp assembly 10 extending from a housing 11. The housing 11 is mounted to an aperture in the side wall W of a fluid treatment chamber, such that the lamp assembly 10 extends into the chamber. The lamp assembly 10 comprises a low or medium pressure lamp 12 contained within a protective quartz glass sleeve 13, which is closed at its distal end. A second or outer tubular sleeve 14 of Teflon® FEP is positioned around the side wall of the first sleeve 13 and an annular cavity 15 extends between the two sleeves. Annular clamps 16 are provided at opposite ends of the sleeve 14 to secure the latter to the sleeve 13 and seal the cavity 15.

The proximal end of the sleeve 13 is sealed to the housing 11 by a compressible o-ring 17 fitted over the end of the sleeve 13. The o-ring 17 is compressed against the sleeve 13 by a ring clamp 18 to trap the outer sleeve 13 and provide a fluid tight seal between the outer sleeve 13 and the cylindrical housing 11.

An annular duct 19 extends around the sleeve 13 through the housing 11 and opens into the cavity 15 formed between the inner and outer sleeves 13,14. An inlet/outlet duct 20 extends radially through the housing 11 from the annular duct 19 and a port 21 is provided at the radially outer end of the duct 20.

In use, the lamp 12 is driven by a suitable ballast circuit and radiation in the germicidal wavelengths 220–280 nm radiates through the inner and outer sleeves 13,14 into the waste water contained in the treatment chamber, both sleeves being transparent or substantially transparent to UV within this wavelength range.

An air supply connected to port 21 introduces filtered air via the ducts 19,20 into the cavity 15 formed between the inner and outer sleeves 13,14. The air pressure is adjusted to be greater than the pressure of the surrounding waste water. The pressure forces the air to flow through the pores of the outer sleeve 14, thereby providing a continuous stream of air over the outer surface of the outer sleeve 14. This continuous flow of air through the pores of the outer sleeve 14 and hence over the outer surface of the sleeve 14, keeps the outer surface of the sleeve clean by preventing contaminants and fouling approaching its surface. The action also helps to purge accumulated contaminants.

If the pressure inside the cavity 15 is adjusted to be less than the pressure of the surrounding waste water, the waste water permeates through the pores of the outer sleeve 14, which acts to filter the water. Any contaminants in the water are retained on the outer surface of the sleeve 14 where they are irradiated and any microorganisms contained therein are killed. The contaminants retained on the outer surface of the sleeve 13 by the this filtering action can be removed by applying pressure to the cavity 15 which is greater than the pressure of the surrounding medium.

Referring to FIG. 2 of the drawings, there is shown an alternative embodiment of this invention which is similar to the embodiment of FIG. 1 and like parts are given like reference numerals. In this alternative embodiment, the inner quartz glass sleeve 13 is open at both ends and sealingly extends between the opposite side walls of a treatment chamber 30.

In use, waste water flows between an inlet 31 and an outlet 32 of the chamber 30 whilst pressurised air is applied to the port 21 in the aforementioned manner.

A UV disinfection lamp devices in accordance with this invention are relatively simple in construction and yet are able to treat waste water reliably for prolonged periods without maintenance and without any substantial loss in their germicidal properties.

The invention claimed is:

1. An irradiation device for emitting radiation through an outer wall thereof formed of a material which is transparent, or substantially transparent, to wavelengths of emitted radiation, said outer wall being formed of a material permeable to fluid, the irradiation device further comprising means for varying the fluid pressure behind an inner surface of said outer wall for causing fluid to, initially, permeate through said outer wall toward, and through, the inner surface of said outer wall in a forward direction and, then, to permeate through said outer wall in a reverse direction back into a fluid medium that is being irradiated.

2. A device as claimed in claim 1, in which said pressure varying means varies said fluid pressure, behind said inner surface of said outer wall, between a pressure which is greater than the pressure of said fluid medium in contact with the outer surface of said outer wall, and a pressure which is lower than the pressure of said fluid medium for causing fluid to alternately permeate through said outer wall in said forward direction and said reverse direction.

3. A device as claimed in claim 1, in which said pressure-varying means comprises a source of fluid under pressure, which communicates with a space behind said inner surface of said outer wall.

4. A device as claimed in claim 3, in which said pressure-varying means further comprises means for adding a cleaning fluid to the fluid passing to said space from said source.

5. A device as claimed in claim 3, further comprising means for heating or cooling the fluid passing to said space from said source.

6. A device as claimed in claim 3, further comprising means for filtering the fluid passing to said space from said source.

7. A device as claimed in claim 1, further comprising an elongate irradiation source, said outer wall being in the form of a sleeve surrounding said irradiation source.

8. A device as claimed in claim 7, in which said sleeve surrounds an inner sleeve which surrounds said irradiation source, a space being formed between the two sleeves and said pressure-varying means varying the pressure within said space.

9. A device as claimed in claim 1, in which said outer wall is formed of PTFE.

* * * * *